US007771448B2

(12) United States Patent
Ravikumar

(10) Patent No.: US 7,771,448 B2
(45) Date of Patent: Aug. 10, 2010

(54) CATHETER DEVICE AND METHOD FOR SELECTIVE OCCLUSION OF ARTERIES OF THE DESCENDING AORTA

(75) Inventor: Sundaram Ravikumar, Briarcliff Manor, NY (US)

(73) Assignee: Arvik Enterprises, LLC, Dobbs Ferry, NY (US)

( * ) Notice: Subject to any disclaimer, the term of this patent is extended or adjusted under 35 U.S.C. 154(b) by 1742 days.

(21) Appl. No.: 10/872,909

(22) Filed: Jun. 21, 2004

(65) Prior Publication Data
US 2005/0283181 A1    Dec. 22, 2005

(51) Int. Cl.
*A61M 29/00*    (2006.01)
(52) U.S. Cl. ........................................ 606/194
(58) Field of Classification Search ............ 606/194
See application file for complete search history.

(56) References Cited

U.S. PATENT DOCUMENTS

| | | | | | |
|---|---|---|---|---|---|
| 4,404,971 | A | * | 9/1983 | LeVeen et al. | 606/194 |
| 4,708,140 | A | | 11/1987 | Baron | 128/325 |
| 5,312,344 | A | | 5/1994 | Grinfield et al. | 604/101 |
| 5,320,605 | A | | 6/1994 | Sahota | 604/101 |
| 5,458,574 | A | | 10/1995 | Machold et al. | 604/101 |
| 5,505,701 | A | * | 4/1996 | Anaya Fernandez de Lomana | 604/101.03 |
| 5,810,757 | A | | 9/1998 | Sweezer, Jr. et al. | 604/4 |
| 5,820,593 | A | | 10/1998 | Safar et al. | 604/96 |
| 6,148,222 | A | * | 11/2000 | Ramsey, III | 600/380 |

(Continued)

FOREIGN PATENT DOCUMENTS

WO    WO 01/19442    9/1999

OTHER PUBLICATIONS

"A New Triple-Balloon, Four-Channel Vascular Catheter for Use in Renal Transplantation", Gill, et al., May 1994, The Journal of Urology; vol. 151, 1416-1419.

(Continued)

*Primary Examiner*—Nicholas D Lucchesi
*Assistant Examiner*—Jason Flick
(74) *Attorney, Agent, or Firm*—Gordon & Jacobson, PC

(57) ABSTRACT

An improved catheter device includes an elongate shaft having a distal portion adapted to be disposed with the abdominal aorta and a plurality of expandable members disposed thereon. One expandable member is dimensioned and configured so that it rests within the iliac bifurcation when expanded. At least two expandable members are spaced apart from the one expandable member and configured to selectively occlude blood flow to different abdominal/pelvic arteries when expanded. Preferably, the distal-most and the proximal-most expandable members are spaced apart at a distance more than 20 cm and less than 40 cm (and most preferably on the order of 30 cm). The expandable members are preferably realized by four inflatable balloons controlled by fluidic pressure supplied thereto via corresponding inflation lumens in the shaft. The catheter device can be fixated within the abdominal aorta and manipulated in order to quickly and efficiently identify and isolate a hemorrhage flowing from an abdominal artery. In another aspect, the catheter device can be used in treating an abdominal aortic aneurysm.

30 Claims, 6 Drawing Sheets

U.S. PATENT DOCUMENTS

| | | | |
|---|---|---|---|
| 6,148,825 A * | 11/2000 | Anderson et al. | 128/898 |
| 6,165,196 A | 12/2000 | Stack et al. | 606/194 |
| 6,565,552 B1 | 5/2003 | Barbut | 604/507 |
| 6,585,689 B1 | 7/2003 | Macoviak et al. | 604/103.07 |
| 6,719,724 B1 * | 4/2004 | Walker et al. | 604/113 |
| 7,335,192 B2 * | 2/2008 | Keren et al. | 604/509 |
| 2001/0001806 A1 | 5/2001 | Turnlund et al. | |
| 2007/0135793 A1 * | 6/2007 | Barbut et al. | 604/509 |

OTHER PUBLICATIONS

"Use of the Intra-Aortic Balloon Pump to Stop Gastrointestinal Bleeding"; by CD Karkos, IA Brue, and ME Lambert; Sep. 2001; Ann Emerg. Med. 2001, (Jan. 2001).

"Intra-aortic Balloon Pump"; Cardiology in Critical Care; IABP; downloaded from Internet at Http://rnbob.tripod.com/iabp.htm Apr. 30, 2004.

* cited by examiner

CATHETER DEVICE AND METHOD FOR SELECTIVE OCCLUSION OF ARTERIES OF THE DESCENDING AORTA

BACKGROUND OF THE INVENTION

1. Field of the Invention

This invention relates broadly to occlusion catheter devices and associated methods for vascular applications. More particularly, this invention relates to aortic occlusion catheter devices and associated methods.

2. State of the Art

Hemorrhagic shock is typically the result of penetrating injuries such as caused by traffic accidents and gunshot wounds. When a patient is suffering from hemorrhagic shock, cardiac function is unimpaired and the cause of the shock is blood loss. Treatment of hemorrhagic shock consists of volume replacement and hemostasis. In many trauma situations, it may be difficult to isolate the injury that is the cause of the loss of blood. In these situations, maintaining blood flow to the heart, neck and lungs while temporarily blocking the flow of blood through the aorta may be necessary to stabilize the patient and provide time for interventional treatment.

An example of such treatment is described in U.S. Pat. No. 5,820,593 wherein an aortic balloon catheter is inserted into the femoral artery and guided into position in the aorta of the patient. The balloon catheter includes two balloons, a distal balloon and a proximal balloon. The distal balloon is positioned in the ascending aorta just above the aortic valve. The proximal balloon is positioned in the descending aorta below the brachiocephalic trunk. When only the proximal balloon is inflated, a supply of blood is delivered to the arteries of the head and heart while blocking the flow of blood below the thorax, thereby providing hemostasis in severe hemorrhage below the thorax. However, these prior art devices and treatments require opening the intra-abdominal cavity and manually inspecting the arteries of the intra-abdominal cavity (many of which are hidden behind the organs therein) in order to identify the root cause of the hemorrhage. Once the cause of the hemorrhage is identified, the injured artery is clamped upstream from the injury. These steps are typically time consuming and can be problematic, especially when there is severe bleeding. In these cases, the lack of blood flowing below the thorax can result in renal failure or damage to other parts of the body that rely on blood flowing below the thorax.

Thus, there remains a need in the art to provide devices and treatments that provide for quick identification and isolation of an injured artery below the thorax, thereby stabilizing the patient and providing time for interventional treatment.

SUMMARY OF THE INVENTION

It is therefore an object of the invention to provide a surgical device (and corresponding method of treatment) that enables quick identification and isolation of a hemorrhaging artery in the abdomen/pelvis (e.g., below the thorax), thereby allowing the attending physician to stabilize the patient and provide time for interventional treatment.

It is another object of the invention to provide a surgical device (and corresponding method of treatment) that enables quick identification and isolation of a hemorrhaging artery in the abdomen/pelvis without requiring that the abdominal cavity be opened for inspection and clamping.

It is a further object of the invention to provide a surgical device (and corresponding method of treatment) that selectively occludes the arteries flowing from the abdominal aorta in a manner that stabilizes the blood pressure of the patient while maintaining blood flow through arteries that are upstream from the hemorrhage.

It is also an object of the invention to provide a surgical device (and corresponding method of treatment) that is quickly and effectively located (e.g., secured in place) in the abdominal aorta of the patient.

In accord with these objects, which will be discussed in detail below, an improved catheter device for accessing the abdominal aorta of a patient includes an elongate hollow catheter shaft which is advanceable though the arterial system of the patient. The catheter shaft has a proximal portion that extends out from the patient and a distal portion adapted to be disposed within the abdominal aorta of the patient. A plurality of expandable members are disposed on the distal portion. One expandable member is dimensioned and configured so that it rests within the iliac bifurcation of the abdominal aorta when expanded so as to secure the catheter and minimize catheter movement within the abdominal aorta of the patient. At least two other expandable members are spaced apart from the one expandable member and configured to selectively occlude blood flow to different arteries that extend from the abdominal aorta when expanded. Preferably, the distal-most and the proximal-most expandable members are spaced apart at a distance of more than 20 cm and less than 40 cm (and most preferably on the order of 30 cm).

The improved catheter device of the present invention can be quickly fixatted within the abdominal aorta and manipulated in order to efficiently identify and isolate a hemorrhage flowing from an abdominal artery. In addition, the improved catheter device can be used in treating an abdominal aortic aneurysm.

According to a preferred embodiment of the invention, the expandable members are realized by four inflatable balloons controlled by fluidic pressure supplied thereto via corresponding inflation lumens in the elongate catheter shaft. The balloons are independently inflatable to a diameter of at least 2.5 cm, and the catheter shaft has an external diameter in a range between 7 and 9 french with a total length of at least 80 cm.

Additional objects and advantages of the invention will become apparent to those skilled in the art upon reference to the detailed description taken in conjunction with the provided figures.

DETAILED DESCRIPTION OF THE PREFERRED EMBODIMENTS

The descriptive terms "downstream" and "upstream", when used herein in relation to the patient's vasculature, relate to the direction of normal blood flow and to the direction opposite normal blood flow, respectively, i.e., "upstream" is closer to the heart in the arterial system.

In addition, the terms "proximal" and "distal", when used in relation to instruments used in a surgical procedure refer to directions closer and farther away, respectively, from that end of the instrument which is held or manipulated by the operator performing the procedure.

Figure 1:
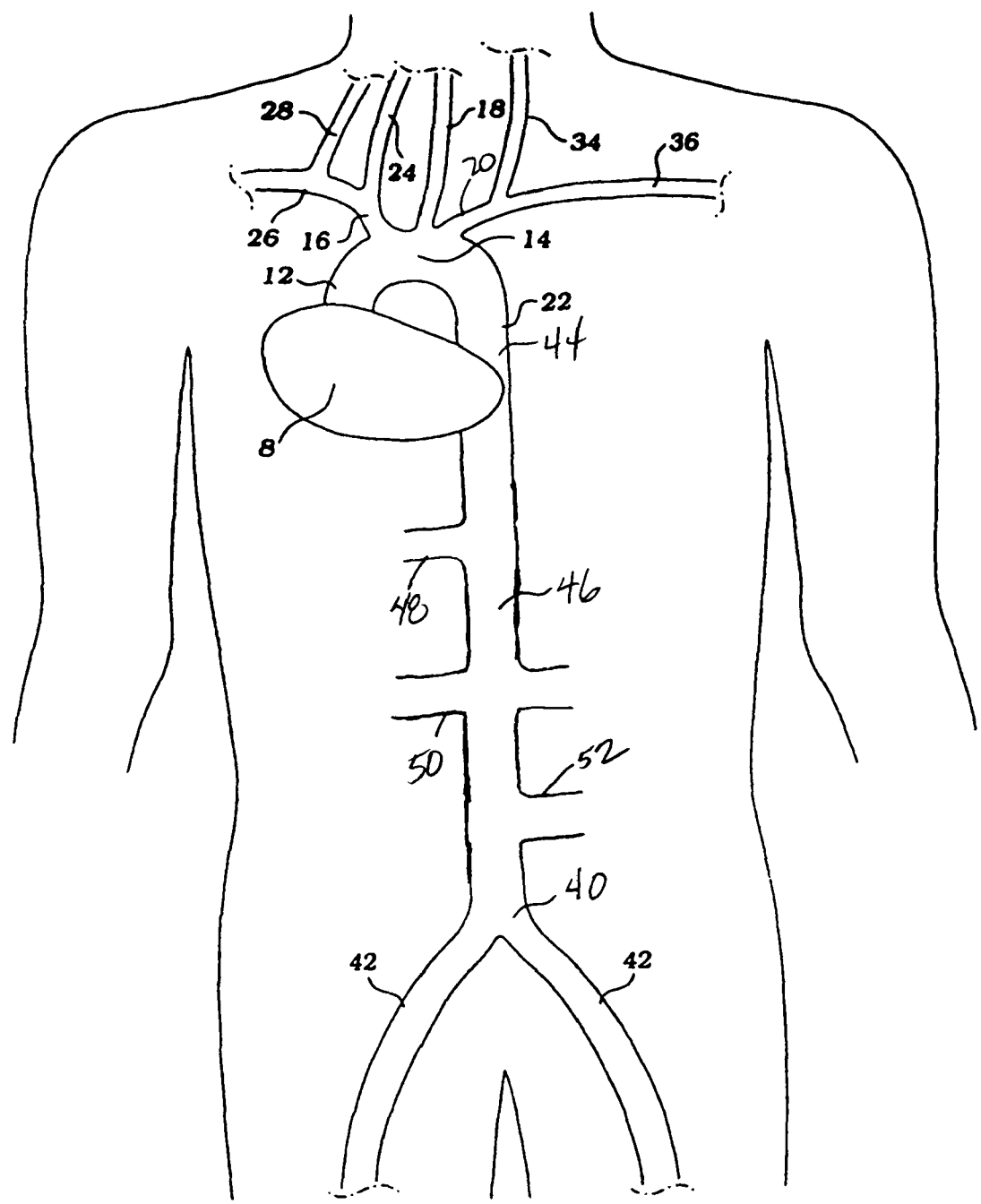
FIG. 1 is a schematic illustration of the principle arteries of the human body.

The principle arteries of the human body are shown in FIG. 1. During systole, oxygenated blood leaves the heart 8 and enters the aorta 10. The aorta 10 includes the ascending aorta 12, the aortic arch 14, and the descending aorta 22. The aortic arch 14 leads to the brachiocephalic trunk 16, the left common carotid artery 18, and the left subclavian artery 20. The brachiocephalic trunk 16 branches into the right common carotid artery 24 and the right subclavian artery 26. The right and left subclavian arteries 26, 20 give rise to the right vertebral artery 28 and the left vertebral artery 34, respectively in addition to the right auxiliary artery 26 and the left auxiliary artery 36, respectively. The descending aorta 22 starts after the aortic arch 14 and ends at the iliac bifurcation 40, which is a branch that splits into the two common iliac arteries 42 that go to the legs.

The descending aorta 22, by convention, is subdivided into the thoracic aorta 44 and the abdominal aorta 46. The thoracic aorta 44 runs from the aortic arch 14 to the diaphragm and gives off numerous branches that supply oxygenated blood to the chest cage and the organs within the chest. The abdominal aorta 46 begins at the diaphragm as a continuation of the thoracic aorta 44 and runs down to the iliac bifurcation 40. The abdominal aorta supplies oxygenated blood to all of the abdominal and pelvic organs and the legs.

The abdominal aorta 46 leads to the celiac artery 48, the superior mesenteric and renal arteries 50, and the inferior mesenteric artery 52. The celiac artery 48 is a short thick branch of artery about an inch in length that divides into three branches, the gastric, hepatic, and splenic arteries. The celiac artery 48 supplies blood to the intestines, spleen, and liver. The superior mesenteric artery supplies blood to the intestines, and the renal arteries supply blood to the kidneys. The inferior mesenteric artery 52 supplies blood to the colon and the rectum.

Figure 2A:
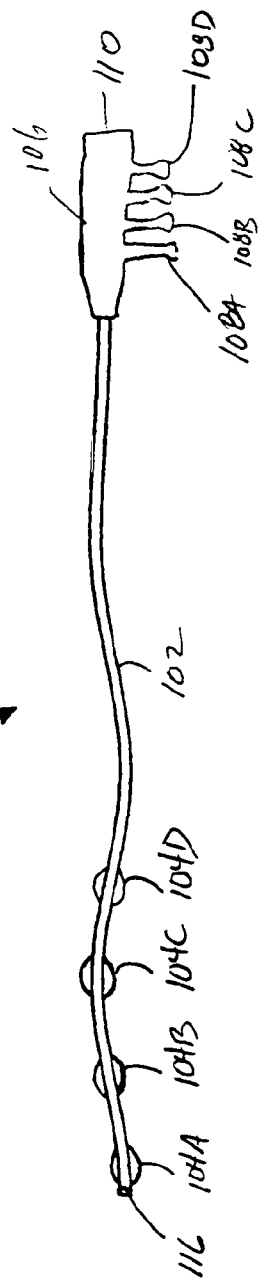
FIG. 2A is a side view of an illustrative embodiment of a catheter device in accordance with the present invention.
Figure 2B:
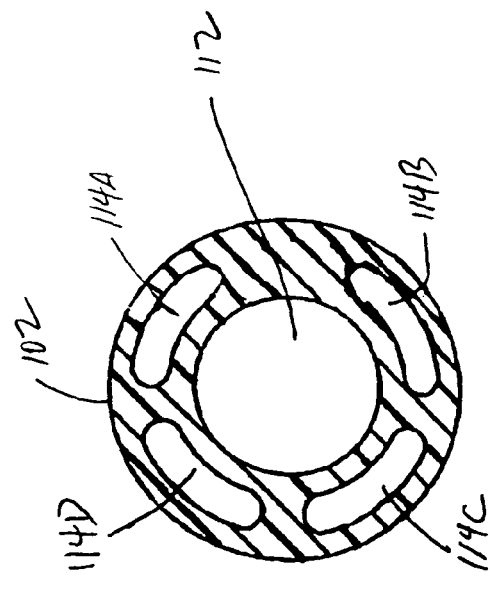
FIG. 2B is a cross-sectional view of the catheter shaft of the catheter device of FIG. 2A.

FIGS. 2A and 2B depict an aortic occlusion catheter device 100 in accordance with the present invention. The device 100 includes a hollow elongate catheter shaft 102 with four distally-mounted expandable occlusion balloons 104A, 104B, 104C, 104D. The four occlusion balloons are spaced apart along the distal portion of the shaft 102. Preferably, the balloons are expandable to a maximum diameter of approximately 2.5 to 3 cm, and the spacing between adjacent balloons is regular at a distance of approximately 10 cm. In this configuration, there is a distance on the order of approximately 30 cm between the first balloon 104A and the fourth balloon 104D. These dimensions correspond to the configuration and spacing of the major arteries (e.g., the celiac artery 48, renal arteries and superior mesenteric artery 50, inferior mesenteric artery 52, iliac bifurcation 40) of the abdominal aorta 46 as will become evident from the operation of the catheter device 100 as set forth below.

The proximal end of the catheter device 100 is provided with a multi-port adapter 106. The adapter 106 has four ports 108A, 108B, 108C, 108D and a main access port 110. The first port 108A is in fluid communication with the first balloon 104A. The second port 108B is in fluid communication with the second balloon 104B. The third port 108C is in fluid communication with the third balloon 104C. The fourth port 108D is in fluid communication with the fourth balloon 104D. The main access port 110 is in fluid communication with a distal port 116 on the distal end of the catheter shaft 102.

As shown in FIG. 2B, the hollow elongate catheter shaft 102 has a main inner lumen 112 and four inflation lumens 114A, 114B, 114C, 114D. The main lumen 112 extends in fluid communication between the main access port 110 and the distal port 116. The first inflation lumen 114A extends in fluid communication between the first port 108A and the first balloon 104A. The second inflation lumen 114B extends in fluid communication between the second port 108B and the second balloon 104B. The third inflation lumen 114C extends in fluid communication between the third port 108C and the third balloon 104C. The fourth inflation lumen 114D extends in fluid communication between the fourth port 108D and the fourth balloon 104D. The four inflation lumens 114A, 114B, 114C, 114D allow for independent inflation and deflation of the four balloons 104A, 104B, 104C, 104D by pumping a fluid (such as a saline solution or air or other medium) into and from the balloons via the ports 108A, 108B, 108C, 108D, respectively.

The main lumen 112 and the distal port 116 may be used to pass a wide variety of surgical devices (such as guide wires, angioscopes, irrigation lines, aortic grafts and the like) into the aorta of the patient. The catheter shaft 102 may also include an additional port and lumen (not shown) that are in fluid communication with one another. The port and lumen are also in fluid communication with an aperture (not shown) in the catheter shaft. The aperture is disposed upstream with respect to the four balloons 104A, 104B, 104C, 104D. These elements provide a manometer for measuring the upstream pressure within the aorta. A pressure monitor is attached the port to monitor the upstream pressure within the aorta.

The catheter shaft 102 preferably has an external diameter between 7 and 9 french such that it can be introduced into the left subclavian artery 20 (or possibly the left common carotid artery 18, the brachiocephalic trunk 16, the right common carotid artery 24, or the right subclavian artery 26) and advanced through the aortic arch 14 and down into the abdominal aorta 46. Alternatively, the catheter shaft 102 may be introduced into a femoral artery and advanced from below into the abdominal aorta 46. The spacing of the four balloons 104A, 104B, 104C, 104D along the distal portion of the catheter shaft 102 allows the balloons to be positioned in the abdominal aorta 46. This will generally require that the length of the catheter shaft 102 be at least 80 cm, and preferably about 90-100 cm. As described below in detail, the first balloon 104A (or the last balloon 104D) is inflated and located at the iliac bifurcation 40, and thus acts to fix the position of the catheter device 100 in the abdominal aorta 46. In this manner the first balloon 104A (or the last balloon 104D) secures the catheter device 100 and minimizes catheter movement within the abdominal aorta 46. The other balloons are inflated and/or deflated as desired in order to maintain pressure in the abdominal aorta 46 and thus stabilize the patient.

The catheter shaft 102 may be formed of conventional polymers (e.g., polyethelene, polyvinyl chloride, PTFE, PEBAX® and the like. The occluding balloons may be formed of conventional polymer sheet material and the like as is well known in the art. The catheter shaft 102 and/or the occluding balloons 104A, 104B, 104C, 104D may incorporate radio-opaque material to facilitate advancement and placement of the catheter utilizing fluoroscopic imaging techniques.

Figure 3:
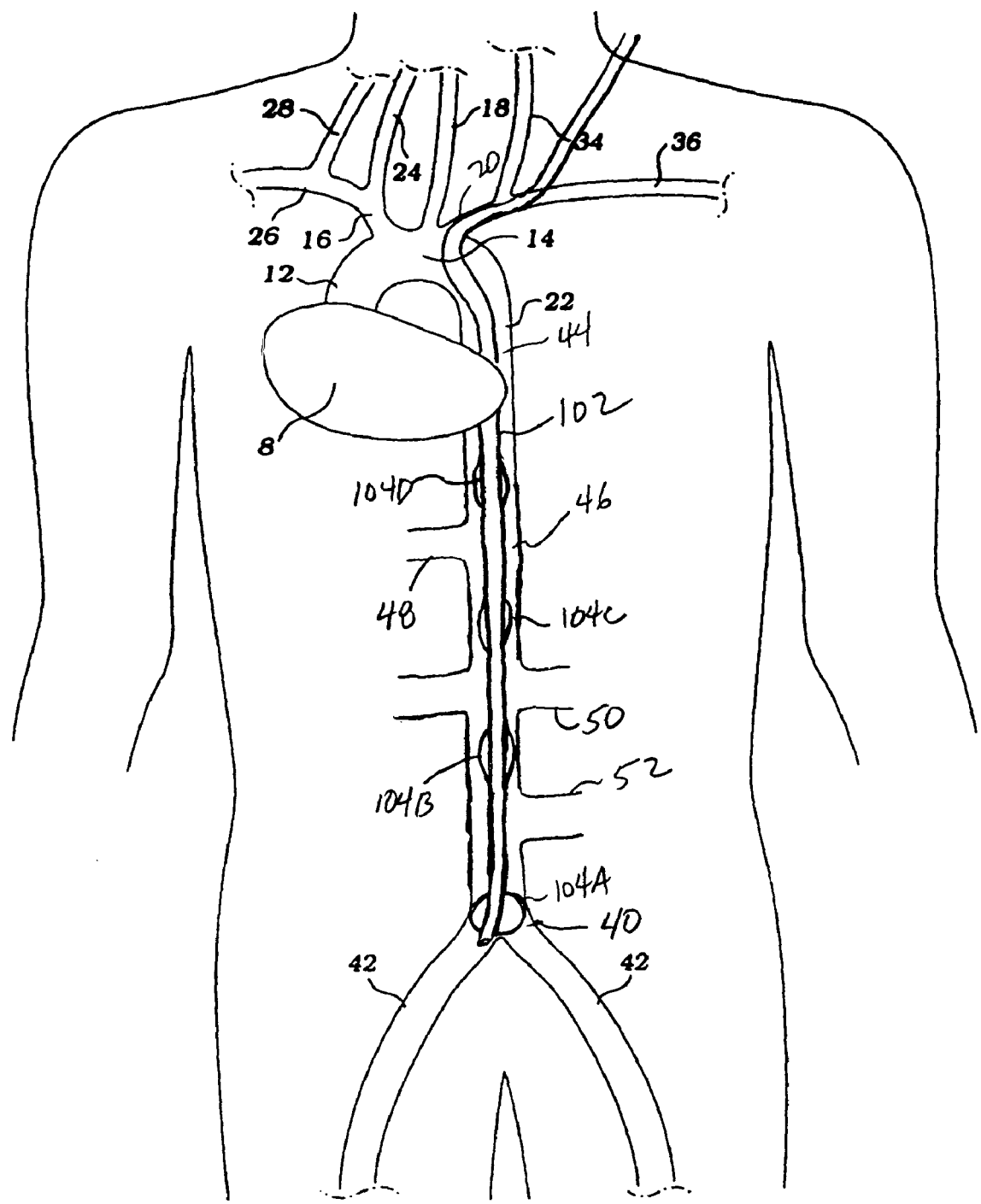
FIG. 3 is a schematic illustration showing the advancement and placement of the catheter device of FIGS. 2A and 2B into the abdominal aorta via the subclavian artery during treatment for hemorrhagic shock in accordance with the present invention.

FIG. 3 illustrates the aortic catheter 100 with the occluding balloons 104A, 104B, 104C, 104D disposed with the patient's abdominal aorta 46. The catheter shaft 102 is introduced into the left subclavian artery 20 and advanced through the aortic arch 14 and down into the abdominal aorta 46. The first balloon 104A is inflated (as shown) and then the catheter shaft 102 is moved distally such that the first balloon 104A is positioned at the iliac bifurcation 40 as shown. In this manner, the first balloon 104A, when inflated, fixes the position of the catheter device 100 in the abdominal aorta 46 and also occludes blood from flowing through the iliac bifurcation. This configuration enables quick and efficient fixation of the aortic catheter device 100, which is advantageous in trauma situations where the patient is experiencing excessive internal bleeding.

After the catheter device 100 is fixed in position (e.g., with the first balloon 104A located at the iliac bifurcation 40), the other three balloons 104B, 104C, 104D are inflated and/or deflated as desired in order to identify and isolate a hemorrhage flowing from an artery in the abdominal aorta 46 and thus stabilize the patient.

More particularly, the second balloon 104B may be inflated to occlude blood from flowing downstream with respect to the balloon 104B. Because the second balloon 104B is positioned upstream from the inferior mesenteric artery 52, such occlusion blocks the flow of blood flowing through the inferior mesenteric artery 52. Similarly, the third balloon 104C may be inflated to occlude blood from flowing downstream with respect to the balloon 104C. Because the third balloon 104C is positioned upstream from the inferior mesenteric artery 52 and the superior mesenteric and renal arteries 50, such occlusion blocks the flow of blood flowing through the inferior mesenteric artery 52 as well as the superior mesenteric and renal arteries 50. Finally, the fourth balloon 104D may be inflated to occlude blood from flowing downstream with respect to the balloon 104D. Because the fourth balloon 104D is positioned upstream from the inferior mesenteric artery 52, the superior mesenteric and renal arteries 50 and the celiac artery 48, such occlusion blocks the flow of blood flowing through the inferior mesenteric artery 52, the superior mesenteric and renal arteries 50 as well as the celiac artery 48.

Note that when the fourth balloon 104D is pressurized to a level that does not occlude the flow of blood downstream therefrom, blood is pumped into the celiac artery 48 during systole. When the third and fourth balloons 104C, 104D are pressurized to a level that does not occlude the flow of blood downstream therefrom, blood is pumped into the celiac artery 48 and into the superior mesenteric and renal arteries 50 during systole. When the second, third and fourth balloons 104B, 104C, 104D are pressurized to a level that does not occlude the flow of blood downstream therefrom, blood is pumped into the celiac artery 48, the superior mesenteric and renal arteries 50 and the inferior mesenteric artery 52 during systole. Finally, when the first, second, third and fourth balloons 104A, 104B, 104C, 104D are pressurized to a level that does not occlude the flow of blood downstream therefrom, blood is pumped into the celiac artery 48, the superior mesenteric and renal arteries 50, the inferior mesenteric artery 52 and the iliac arteries 42 during systole.

As described above with respect to FIG. 3, the aortic catheter 100 of the present invention can be used to quickly identification and isolate a hemorrhage flowing from an artery in the abdominal aorta 46. Preferably, this is accomplished as follows:

i) introduce the catheter shaft into the left subclavian artery and advance it through the aortic arch and down into the abdominal aorta, and then inflate the first balloon 104A and move the catheter device distally in order to locate the first balloon 104A at the iliac bifurcation 40;

ii) if need be, adjust the inflation level of the first balloon 104A such that it blocks blood from flowing downstream through the iliac arteries;

iii) monitor the aortic pressure at a position upstream from the four balloons 104A, 104B, 104C, 104D;

iv) if the pressure is normal (i.e., an indication that the hemorrhage has been isolated in the iliac arteries or one or more vessels downstream therefrom), end the manipulation of the occlusion of the four balloons and continue monitoring the stability of the patient; surgical procedures are performed to identify and repair the injured artery, which typically requires opening up the abdominal cavity, locating the injured artery and then repairing the injured artery;

v) if the pressure is low (i.e., an indication that the hemorrhage has not been isolated), adjust the inflation level of the fourth balloon 104D such that it blocks blood from flowing downstream therefrom;

vi) monitor the aortic pressure at a position upstream from the four balloons 104A, 104B, 104C, 104D;

vii) if the pressure is low (i.e., an indication that the hemorrhage has not been isolated), it is probable that the source of the hemorrhage is upstream from the abdominal aorta 46 (e.g., within the thoracic aorta 44, the aortic arch 14, the ascending aorta 12 or vessels downstream therefrom); end the manipulation of the occlusion of the four balloons and continue monitoring the stability of the patient; surgical procedures are undertaken to identify and isolate the source of such bleeding utilizing other means.

viii) if the pressure is normal, adjust the inflation level of the third balloon 104C such that it blocks blood from flowing downstream, and adjust the inflation level of the fourth balloon 104D such that it does not block blood from flowing downstream therefrom; this configuration allows blood to flow downstream into the celiac artery.

ix) monitor the aortic pressure at a position upstream from the four balloons 104A, 104B, 104C, 104D;

x) if the pressure is low (i.e., an indication that the hemorrhage is flowing from the celiac artery), adjust the inflation level of the fourth balloon 104D such that it blocks blood from flowing downstream, thereby isolating the hemorrhage; end the manipulation of the occlusion of the four balloons and continue monitoring the stability of the patient; surgical procedures are performed to identify and repair the injured artery, which typically requires opening up the abdominal cavity, locating the injured artery and then repairing the injured artery;

xi) if the pressure is normal, adjust the inflation level of the second balloon 104B such that it blocks blood from flowing downstream, and adjust the inflation levels of the fourth balloon 104D and third balloon 104C such that they do not block blood from flowing downstream, if need be; this configuration allows blood to flow downstream into the renal arteries and upper mesenteric artery.

xii) monitor the aortic pressure at a position upstream from the four balloons 104A, 104B, 104C, 104D;

xiii) if the pressure is low (i.e., an indication that the hemorrhage is flowing from the renal arteries/upper mesenteric artery), adjust the inflation level of the third balloon 104C such that it blocks blood from flowing downstream, thereby isolating the hemorrhage; end the manipulation of the occlusion of the four balloons and continue monitoring the stability of the patient; surgical treatment is then performed to identify and repair the injured artery, which typically requires opening up the abdominal cavity, locating the injured artery and then repairing the injured artery; and xiv) if the pressure is normal (i.e., an indication that the hemorrhage is flowing from the lower mesenteric artery), the inflation level of the second balloon 104B is maintained such that it blocks blood from flowing downstream, thereby isolating the hemorrhage; end the manipulation of the occlusion of the four balloons and continue monitoring the stability of the patient; surgical treatment is then performed to identify and repair the injured artery, which typically requires opening up the abdominal cavity, locating the injured artery and then repairing the injured artery.

The sequence of operations set forth in i)-xiv) directly above advantageously provides timely hemostasis, which is typically suitable for critically injured patients. However, it blocks blood flow through the upper arteries of the abdominal cavity (e.g., the celiac and renal arteries), thereby potentially impacting the normal function of the organs (e.g., the liver and/or kidney) that rely on the upper arteries of the abdominal cavity. Thus, in some circumstances (for example, where the blood pressure of the patient is not in a critical condition), an alternate sequence of operations may be used. For example, the balloons 104B, 104C, 104D may be sequentially inflated/deflated in order to isolate the hemorrhage. This sequence of operations potentially minimizes the loss of blood flow through the upper arteries of the abdominal cavity (e.g., the celiac and renal arteries), and thus minimizes the potential impact to the normal function of the organs (e.g., the liver and/or kidney) that rely on the upper arteries of the abdominal cavity.

Figure 4:
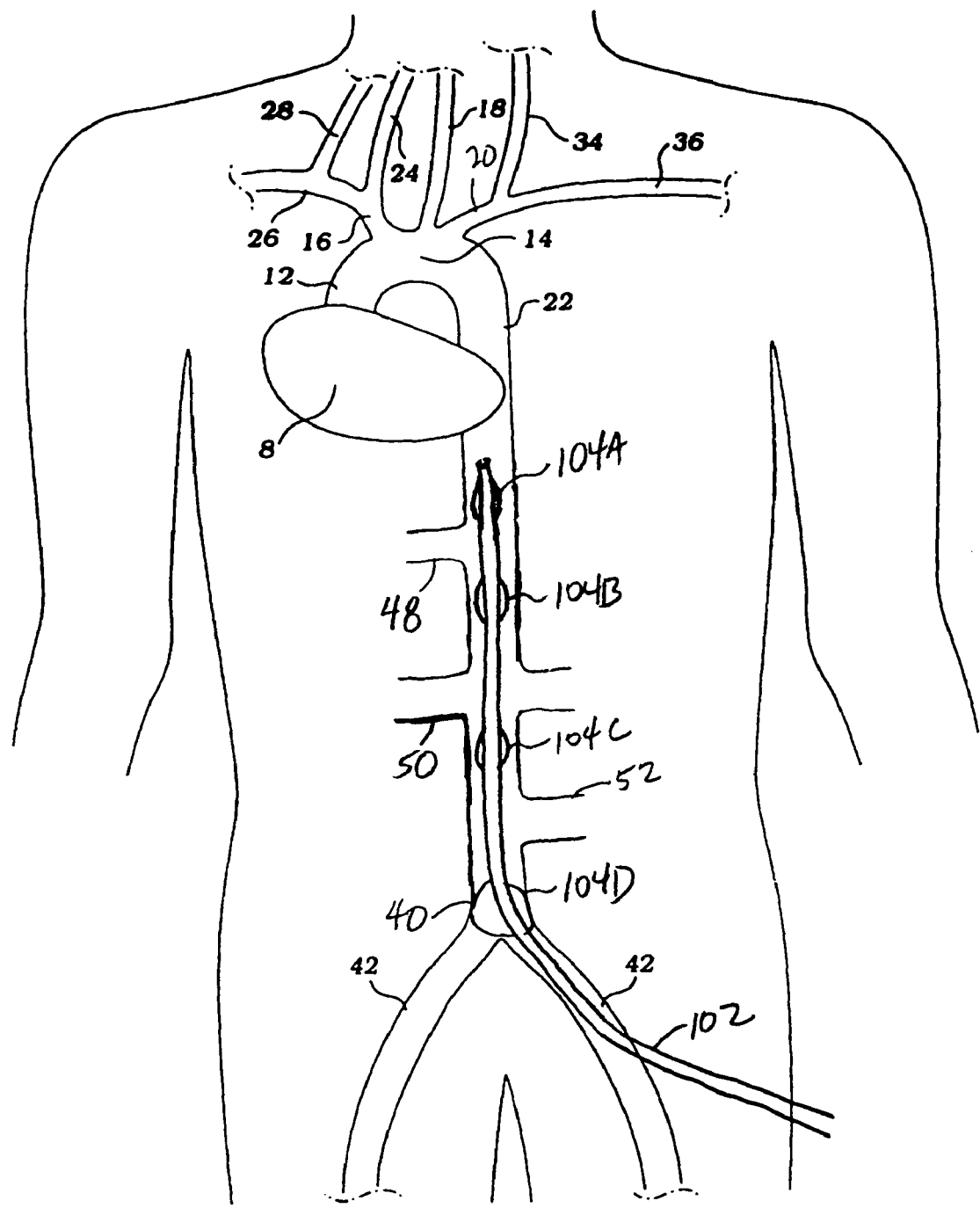
FIG. 4 is a schematic illustration showing the advancement and placement of the catheter device of FIGS. 2A and 2B into the abdominal aorta via the femoral artery during treatment for hemorrhagic shock in accordance with the present invention.

FIG. 4 illustrates the aortic catheter 100 with the balloons 104A, 104B, 104C, 104D disposed with the patient's abdominal aorta 46. The catheter shaft 102 is introduced into the femoral artery and advanced through the iliac bifurcation 40 such that four balloons 104A, 104B, 104C, 104D are positioned in the abdominal aorta 46. The fourth balloon 104D is inflated (as shown) and then the catheter shaft 102 is moved proximally such that the fourth balloon 104D is positioned at the iliac bifurcation 40 as shown. In this manner, the fourth balloon 104D, when inflated, fixes the position of the catheter device 100 in the abdominal aorta 46 and also occludes blood from flowing through the iliac bifurcation. This configuration enables quick and efficient fixation of the aortic catheter device 100, which is advantageous in trauma situations where the patient is experiencing excessive internal bleeding.

After the catheter device 100 is fixed in position (e.g., with the fourth balloon 104D located at the iliac bifurcation 40), the other three balloons 104A, 104B, 104C are inflated and/or deflated as desired in order to identify and isolate a hemorrhage flowing from an artery in the abdominal aorta 46 and thus stabilize the patient.

More particularly, the third balloon 104C may be inflated to occlude blood from flowing downstream with respect to the balloon 104C. Because the third balloon 104C is positioned upstream from the inferior mesenteric artery 52, such occlusion blocks the flow of blood flowing through the inferior mesenteric artery 52. Similarly, the second balloon 104B may be inflated to occlude blood from flowing downstream with respect to the balloon 104B. Because the second balloon 104B is positioned upstream from the inferior mesenteric artery 52 and the superior mesenteric and renal arteries 50, such occlusion blocks the flow of blood flowing through the inferior mesenteric artery 52 as well as the superior mesenteric and renal arteries 50. Finally, the first balloon 104A may be inflated to occlude blood from flowing downstream with respect to the balloon 104A. Because the first balloon 104A is positioned upstream from the inferior mesenteric artery 52, the superior mesenteric and renal arteries 50 and the celiac artery 48, such occlusion blocks the flow of blood flowing through the inferior mesenteric artery 52, the superior mesenteric and renal arteries 50 as well as the celiac artery 48.

Note that when the first balloon 104A is pressurized to a level that does not occlude the flow of blood downstream therefrom, blood is pumped into the celiac artery 48 during systole. When the first and second balloons 104A, 104B are pressurized to a level that does not occlude the flow of blood downstream therefrom, blood is pumped into the celiac artery 48 and into the superior mesenteric and renal arteries 50 during systole. When the first, second and third balloons 104A, 104B, 104C are pressurized to a level that does not occlude the flow of blood downstream therefrom, blood is pumped into the celiac artery 48, the superior mesenteric and renal arteries 50 and the inferior mesenteric artery 52 during systole. Finally, when the first, second, third and fourth balloons 104A, 104B, 104C, 104D are pressurized to a level that does not occlude the flow of blood downstream therefrom, blood is pumped into the celiac artery 48, the superior mesenteric and renal arteries 50, the inferior mesenteric artery 52 and the iliac arteries 42 during systole.

As described above with respect to FIG. 4, the aortic catheter 100 of the present invention can be used to quickly identification and isolate a hemorrhage flowing from an artery in the abdominal aorta 46. Preferably, this is accomplished as follows:

i) introduce the catheter shaft into the renal artery and advance it up into the abdominal aorta, and then inflate the fourth balloon 104D and move the catheter device proximally in order to locate the fourth balloon 104D at the iliac bifurcation 40;

ii) if need be, adjust the inflation level of the fourth balloon 104D such that it blocks blood from flowing downstream through the iliac arteries;

iii) monitor the aortic pressure at a position upstream from the four balloons 104A, 104B, 104C, 104D;

iv) if the pressure is normal (i.e., an indication that the hemorrhage has been isolated in the iliac arteries or one or more vessels downstream therefrom), end the manipulation of the occlusion of the four balloons and continue monitoring the stability of the patient; surgical procedures are performed to identify and repair the injured artery, which typically requires opening up the abdominal cavity, locating the injured artery and then repairing the injured artery;

v) if the pressure is low (i.e., an indication that the hemorrhage has not been isolated), adjust the inflation level of the first balloon 104A such that it blocks blood from flowing downstream therefrom;

vi) monitor the aortic pressure at a position upstream from the four balloons 104A, 104B, 104C, 104D;

vii) if the pressure is low (i.e., an indication that the hemorrhage has not been isolated), it is probable that the source of the hemorrhage is upstream from the abdominal aorta 46 (e.g., within the thoracic aorta 44, the aortic arch 14, the ascending aorta 12 or vessels downstream therefrom); end the manipulation of the occlusion of the four balloons and continue monitoring the stability of the patient; surgical procedures are undertaken to identify and isolate the source of such bleeding utilizing other means.

viii) if the pressure is normal, adjust the inflation level of the second balloon 104B such that it blocks blood from flowing downstream, and adjust the inflation level of the first balloon 104A such that it does not block blood from flowing downstream therefrom; this configuration allows blood to flow downstream into the celiac artery.

ix) monitor the aortic pressure at a position upstream from the four balloons 104A, 104B, 104C, 104D;

x) if the pressure is low (i.e., an indication that the hemorrhage is flowing from the celiac artery), adjust the inflation level of the first balloon 104A such that it blocks blood from flowing downstream, thereby isolating the hemorrhage; end the manipulation of the occlusion of the four balloons and continue monitoring the stability of the patient; surgical procedures are performed to identify and repair the injured artery, which typically requires opening up the abdominal cavity, locating the injured artery and then repairing the injured artery;

xi) if the pressure is normal, adjust the inflation level of the third balloon 104C such that it blocks blood from flowing downstream, and adjust the inflation levels of the first balloon 104A and second balloon 104B such that they do not block blood from flowing downstream, if need be; this configuration allows blood to flow downstream into the renal arteries and upper mesenteric artery.

xii) monitor the aortic pressure at a position upstream from the four balloons 104A, 104B, 104C, 104D;

xiii) if the pressure is low (i.e., an indication that the hemorrhage is flowing from the renal arteries/upper mesenteric artery), adjust the inflation level of the second balloon 104B such that it blocks blood from flowing downstream, thereby isolating the hemorrhage; end the manipulation of the occlusion of the four balloons and continue monitoring the stability of the patient; surgical treatment is then performed to identify and repair the injured artery, which typically requires opening up the abdominal cavity, locating the injured artery and then repairing the injured artery; and xiv). if the pressure is normal (i.e., an indication that the hemorrhage is flowing from the lower mesenteric artery), the inflation level of the third balloon 104C is maintained such that it blocks blood from flowing downstream, thereby isolating the hemorrhage; end the manipulation of the occlusion of the four balloons and continue monitoring the stability of the patient; surgical treatment is then performed to identify and repair the injured artery, which typically requires opening up the abdominal cavity, locating the injured artery and then repairing the injured artery.

The sequence of operations set forth in i)-xiv) directly above advantageously provides timely hemostasis, which is typically suitable for critically injured patients. However, it blocks blood flow through the upper arteries of the abdominal cavity (e.g., the celiac and renal arteries), thereby potentially impacting the normal function of the organs (e.g., the liver and/or kidney) that rely on the upper arteries of the abdominal cavity. Thus, in some circumstances (for example, where the blood pressure of the patient is not in a critical condition), an alternate sequence of operations may be used. For example, the balloons 104C, 104B, 104A may be sequentially inflated/deflated in order to isolate the hemorrhage. This sequence of operations potentially minimizes the loss of blood flow through the upper arteries of the abdominal cavity (e.g., the celiac and renal arteries), and thus minimizes the potential impact to the normal function of the organs (e.g., the liver and/or kidney) that rely on the upper arteries of the abdominal cavity.

Advantageously, the aortic occlusion device 100 of the present invention can be fixated within the abdominal aorta and manipulated in order to quickly and efficiently identify and isolate a hemorrhage flowing from an artery in the abdominal aorta, and thus stabilize the patient. Such operations are beneficial in trauma situations where the patient is experiencing excessive internal bleeding and quick stabilization provides time for interventional treatment.

Figure 5:
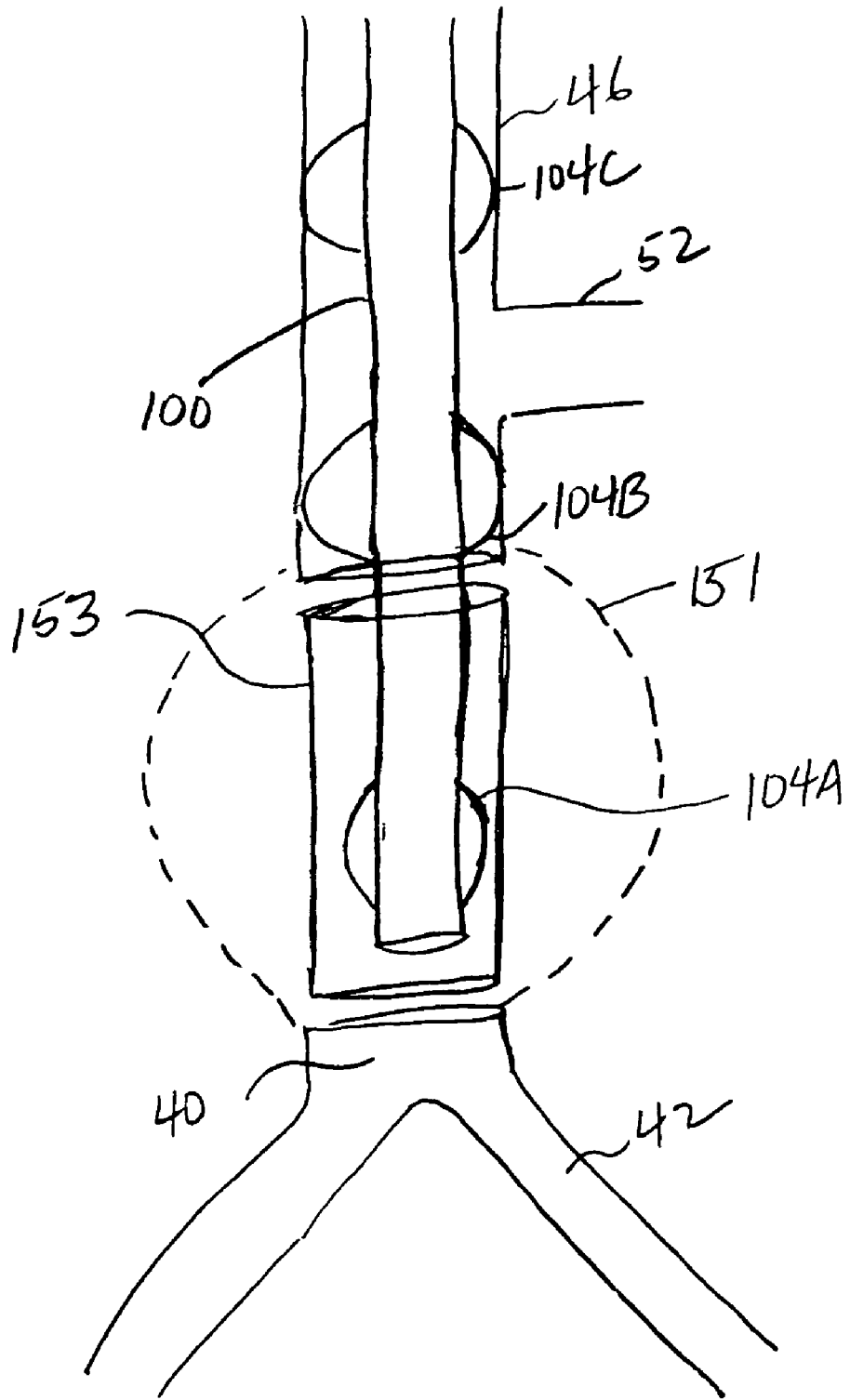
FIG. 5 is a schematic illustration showing the placement of the catheter device of FIGS. 2A and 2B into the abdominal aorta during open surgery of an abdominal aortic aneurysm in accordance with the present invention.

In another aspect of the present invention, the aortic occlusion device 100 can be used in treating an abdominal aortic aneurysm, which is an abnormal ballooning of the abdominal aorta. In such applications, the distal portion of the aortic catheter 100 (with the balloons 104A, 104B, 104C, 104D) is located with the patient's abdominal aorta 46. It may be introduced from above (e.g., into and through the subclavian artery or other artery extending from the aortic arch) as shown in FIG. 5, or introduced from below (e.g., into and through the femoral artery), and advanced into the abdominal aorta as described above. An incision is made into the abdominal cavity and the aneurysm 151 is exposed. One or more of the occlusion balloons of the device 100, which are located upstream from the aneurysm 151, are inflated to a level that occludes the flow of blood downstream, thereby effectively clamping the section of the abdominal aorta 46 that is upstream from the aneurysm 151. The aneurysm 151 is opened and a graft 153 is inserted to bridge the normal aorta above the aneurysm to the normal aorta below the aneurysm. Alternatively, a bifurcated graft may be used to bridge the aorta 46 to the iliac arteries 42. The lumbar arteries may be clamped to prevent back bleeding. A portion of the catheter shaft 102 together with one or more of the occlusion balloons may be disposed within the aneurysm (for example, the part of the catheter shaft supporting balloon 104A as shown in FIG. 5). In this case, before the graft 153 is affixed to the aorta, it may be placed around the outer diameter of that part of the catheter shaft that extends into the aneurysm 151, and the inflatable balloon disposed within the graft 153, if any, may be inflated to temporarily hold the graft 153 in place. In such applications, the four independently inflatable balloons 104A, 104B, 104C, 104D advantageously provide flexibility in occluding various parts of the abdominal aorta 46. Moreover, the quick and efficient fixation of the catheter device 100 within the abdominal aorta can potentially provide time savings during surgery.

Figure 6:
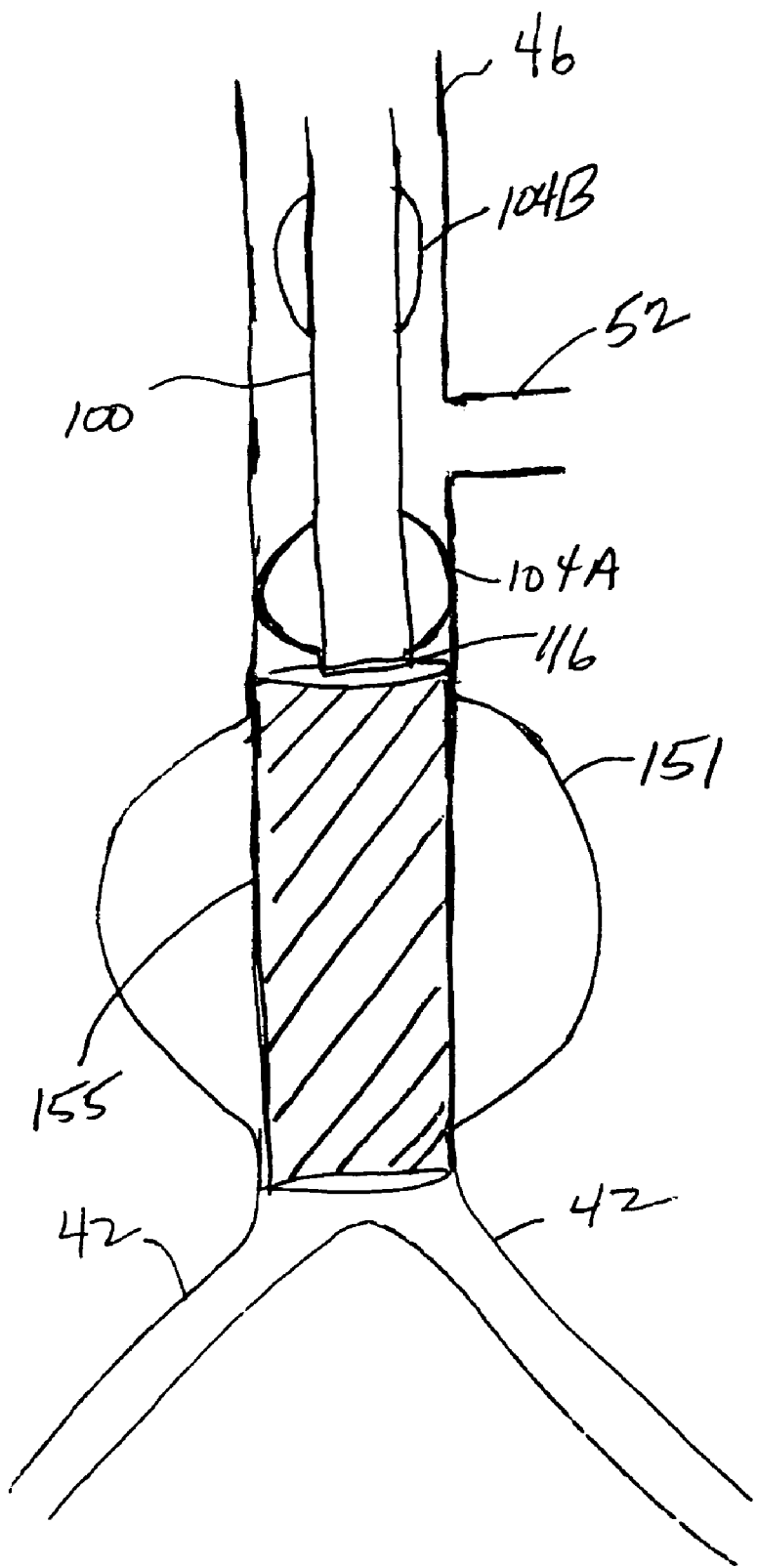
FIG. 6 is a schematic illustration showing the placement of the catheter device of FIGS. 2A and 2B into the abdominal aorta during catheter-based surgery of an abdominal aortic aneurysm in accordance with the present invention.

In yet another aspect of the invention, the aortic occlusion device 100 can be used in a catheter-based treatment of an abdominal aortic aneurysm whereby a stent-graft is seated in the normal aorta above and below the aneurysm, thereby effectively isolating the aneurysm sac from the circulation. In this technique, the stent-graft provides a new normal-sized lumen to maintain blood flow. In such applications, the aortic catheter 100 (with the balloons 104A, 104B, 104C, 104D) is located with the patient's abdominal aorta 46. It may be introduced from above (e.g., into and through the subclavian artery or other artery extending from the aortic arch) as shown in FIG. 6, or introduced from below (e.g., into and through the femoral artery), and advanced into the abdominal aorta as described above. Fluoroscopic imaging techniques are preferably used to locate the distal port 116 of the catheter shaft 102 at the desired position adjacent the aneurysm 151. One or more of the occlusion balloons of the catheter device 100 (e.g., such as the first occlusion balloon 104A as shown) may be inflated to a level that occludes the flow of blood, thereby effectively clamping the abdominal aorta section. The stent-graft 155 is then deployed though the distal port 116 of the catheter device 100, and the catheter device 100 is removed. In such applications, the four independently inflatable balloons 104A, 104B, 104C, 104D advantageously provide flexibility in occluding various parts of the abdominal aorta 46. Moreover, the quick and efficient fixation of the catheter device 100 within the abdominal aorta 46 can potentially provide time savings during surgery.

There have been described and illustrated herein several embodiments of an aortic catheter device with multiple occluding elements and a method of operating the aortic catheter for treating hemorrhagic shock as well as an abdominal aortic aneurysm. While particular embodiments of the invention have been described, it is not intended that the invention be limited thereto, as it is intended that the invention be as broad in scope as the art will allow and that the specification be read likewise. Thus, while particular occluding balloons have been disclosed, it will be appreciated that other occluding elements, such as conical shaped expanding elements or cylindrical-shaped expanding elements, can be used as well. Moreover, the expandable size of such elements can also be controlled by mechanical means such as wires or the like. It is also contemplated that one or more of the occlusion elements can be controlled to partially occlude the aortic passageway. Such partial occlusion may be useful in providing pressure-controlled blood flow to an injured artery after surgically repairing the injured artery. In addition, while a particular configuration of the multi-lumen catheter shaft has been disclosed, it will be appreciated that other multi-lumen configurations, such as a sequence of concentric lumens formed about the inner guide lumen, can be used. Also, while particular configurations and sizes have been disclosed in reference to elements of the aortic catheter, it will be understood that the aortic catheter described herein can be readily adapted to other configurations and sizes. For example, the device can readily be adapted to include more than four (or less than four) occluding elements and supporting inflation lumens/ports. Also, the outside diameter of the device can readily be adapted to different sizes and distances such that the device is suitable for different size patients, such as a smaller diameter catheter for pediatric patients. Similarly, the distance between balloons can readily be adapted. For example, the distance between the distal-most balloon (e.g., first balloon 104A) and the proximal-most balloon (e.g., the fourth balloon 104D) may readily be adapted such that it is in the range between 20 and 40 cm. In another example, the distance separating the balloons may be adapted from that described herein such that the balloons are positioned upstream from different arterial groups with the abdominal aorta. It will therefore be appreciated by those skilled in the art that yet other modifications could be made to the provided invention without deviating from its spirit and scope as claimed.

What is claimed is:

1. A catheter for accessing the abdominal aorta of a patient, comprising:
an elongate catheter shaft which is advanceable though the arterial system of the patient, the catheter shaft having a proximal portion that extends out from the patient and a distal portion adapted to be disposed within the abdominal aorta of the patient; and
a plurality of independently expandable members disposed on said distal portion of said catheter shaft, said expandable members configurable to an expanded state in order to selectively occlude blood flow to different arteries extending from the abdominal aorta of the patient, wherein a first of said expandable members is dimensioned and configured so that it rests within the iliac bifurcation of the abdominal aorta of the patient when configured in its expanded state so as to secure the catheter and minimize catheter movement within the abdominal aorta of the patient, wherein a second of said expandable members is spaced apart from said first expandable member such that it is positioned upstream of the junction of the abdominal aorta and the celiac artery of the patient when said first expandable member rests within the iliac bifurcation, and wherein a third of said expandable members is disposed between said first and second expandable members such that it is positioned upstream from the junction of the renal artery and the abdominal aorta of the patient and downstream from the junction of the celiac artery and the abdominal aorta of the patient when said first expandable member rests within the iliac bifurcation.

2. A catheter according to claim 1, wherein:
said first expandable member is adapted to be configured in an expanded state to thereby selectively occlude blood flow to the iliac arteries of the patient.

3. A catheter according to claim 1, wherein:
said catheter shaft includes a main guide lumen and a plurality of inflation lumens corresponding to said plurality of expandable members.

4. A catheter according to claim 3, further comprising:
a hub disposed on said proximal portion of said catheter shaft, said hub having a main guide port that is in fluid communication with said main guide lumen and a plurality of inflation ports that are in fluid communication with corresponding inflation lumens.

5. A catheter according to claim 3, wherein:
said expandable members are inflatable balloons whose inflation levels are independently controlled by fluidic pressure supplied to said balloons via said inflation lumens.

6. A catheter according to claim 1, wherein:
said first and second expandable members are spaced apart along said distal portion of said catheter shaft at a distance more than 20 cm and less than 40 cm.

7. A catheter according to claim 6, wherein:
said distance is substantially 30 cm.

8. A catheter according to claim 1, wherein:
said expandable members are evenly spaced apart along said distal portion of said catheter shaft.

9. A catheter according to claim 8, wherein:
said expandable members are spaced apart from one another by a distance of approximately 10 cm.

10. A catheter according to claim 1, wherein:
said expandable members comprise a fourth expandable member disposed between said first and second expandable members such that it is positioned upstream from the junction of the inferior mesenteric artery and the abdominal aorta of the patient and downstream from the junction of the renal artery and the abdominal aorta of the patient when said first expandable member rests within the iliac bifurcation.

11. A catheter according to claim 1, wherein:
each of said expandable members are expandable to a diameter of at least 2.5 cm.

12. A catheter according to claim 1, wherein:
said catheter shaft has an external diameter in a range between 7 and 9 french.

13. A catheter according to claim 1, wherein:
said catheter shaft has a total length of at least 80 cm.

14. A catheter comprising:
an elongate catheter shaft having a proximal portion and a distal portion; and
at least four expandable members disposed on said distal portion of said catheter shaft, wherein a distal-most expandable member and a proximal-most expandable member are spaced apart along said distal portion at a distance more than 20 cm and less than 40 cm,
wherein a first expandable member is dimensioned and configured so that it rests within the iliac bifurcation of the abdominal aorta of the patient in an expanded state so as to secure the catheter and minimize catheter movement within the abdominal aorta of the patient,
wherein at least three other expandable members are spaced apart from said first expandable member and configurable to an expanded state to selectively occlude blood flow to different arteries that extend from the abdominal aorta of the patient, and
wherein one of the other expandable members is positioned upstream from the junction of the renal artery and the abdominal aorta of the patient and downstream from the junction of the celiac artery and the abdominal aorta of the patient when said first expandable member rests within the iliac bifurcation.

15. A catheter according to claim 14, wherein:
said distance is substantially 30 cm.

16. A catheter according to claim 14, wherein:
said first expansion member is adapted to be expandable in order to selectively occlude blood flow to the iliac arteries of the patient.

17. A catheter according to claim 14, wherein:
said catheter shaft includes a main guide lumen and at least four inflation lumens corresponding to said at least four expandable members.

18. A catheter according to claim 17, further comprising:
a hub disposed on said proximal portion of said catheter shaft, said hub having a main guide port that is in fluid communication with said main guide lumen and at least four inflation ports that are in fluid communication with said at least four inflation lumens, respectively.

19. A catheter according to claim 17, wherein:
said expandable members are inflatable balloons whose inflation levels are independently controlled by fluidic pressure supplied to said balloons via said inflation lumens.

20. A catheter according to claim 14, wherein:
said expandable members are evenly spaced apart along said distal portion of said catheter shaft.

21. A catheter according to claim 20, wherein:
said expandable members are spaced apart from one another by a distance of approximately 10 cm.

22. A catheter according to claim 14, wherein:
each of said expandable members are expandable to a diameter of at least 2.5 cm.

23. A catheter according to claim 14, wherein:
said catheter shaft has an external diameter in a range between 7 and 9 french.

24. A catheter according to claim 14, wherein:
said catheter shaft has a total length of at least 80 cm.

25. A method of stabilizing pressure in the aorta of a hemorrhagic patient, comprising:

i) providing a catheter device for accessing the abdominal aorta of a patient, the device including an elongate catheter shaft which is advanceable though the arterial system of the patient, the catheter shaft having a proximal portion and a distal portion, and a plurality of independently expandable members disposed on said distal portion of said catheter shaft, wherein a first of said expandable members is configurable into an expanded state whereby it rests within the iliac bifurcation of the abdominal aorta of the patient, and wherein at least two other expandable members are spaced apart from said first expandable member and selectively configurable into an expanded state to occlude blood flow to different arteries that extend from the abdominal aorta of the patient, wherein a particular one of said expandable members is disposed upstream from the junction of the renal artery and the abdominal aorta of the patient and downstream from the junction of the celiac artery and the abdominal aorta of the patient when said first expandable member rests within the iliac bifurcation;

ii) advancing the catheter shaft through the arterial system of the patient such that said distal portion is disposed within the abdominal aorta of the patient;

iii) expanding said first expandable member and moving said catheter shaft such that said first expandable member is seated in the iliac bifurcation of the patient so as to secure the catheter and minimize catheter movement within the abdominal aorta of the patient; and iv) expanding at least one of the two other expandable members to selectively occlude blood flow to at least one artery that extends from the abdominal aorta of the patient in order to isolate the hemorrhage and stabilize pressure within the aorta of the patient, wherein the expanding step iv) expands the particular one expandable member to occlude blood flow to the renal artery of the patient as well as other arteries downstream therefrom.

26. A method according to claim 25, wherein:
said expandable members are inflatable balloons whose inflation levels are independently controlled by fluidic pressure supplied to said balloons via inflation lumens integral to said catheter shaft, and wherein the expanding steps iii) and iv) are accomplished by adjusting fluidic pressure to the respective inflatable balloon to increase the inflation level of the respective balloon.

27. A method according to claim 25, wherein:
another one of said expandable members is disposed upstream from the junction of the inferior mesenteric artery and the abdominal aorta of the patient and downstream from the junction of the renal artery and the abdominal aorta of the patient, and wherein the expanding step iv) expands the particular one expandable member to occlude blood flow to the inferior mesenteric artery of the patient as well as other arteries downstream therefrom.

28. A method according to claim 25, wherein:
another one of said expandable members is disposed upstream from the junction of the celiac artery and the abdominal aorta of the patient, and wherein the expanding step iv) expands the particular one expandable member to occlude blood flow to the celiac artery of the patient as well as other arteries downstream therefrom.

29. A method according to claim 25, further comprising:
introducing said catheter shaft into an artery leading from the aortic arch of the patient, and wherein said catheter shaft is moved distally in order to seat said one expandable member in the iliac bifurcation of the patient.

30. A method according to claim 25, further comprising:
introducing said catheter shaft into the femoral artery of the patient, and wherein said catheter shaft is moved proximally in order to seat said one expandable member in the iliac bifurcation of the patient.

\* \* \* \* \*